United States Patent
Fix et al.

(10) Patent No.: US 9,687,475 B1
(45) Date of Patent: *Jun. 27, 2017

(54) EXTENDED RELEASE PHARMACEUTICAL FORMULATIONS WITH CONTROLLED IMPURITY LEVELS

(71) Applicants: Ezra Pharma LLC, Little Rock, AR (US); Rubicon Research Private Limited, Mumbai (IN)

(72) Inventors: Joseph A. Fix, Lawrence, KS (US); Shirish A. Shah, Phoenix, AZ (US); Pratibha S. Pilgaonkar, Mumbai (IN); Anilkumar S. Gandhi, Mumbai (IN)

(73) Assignees: Ezra Pharma LLC, Little Rock, AR (US); Rubicon Research Private Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,305

(22) Filed: Mar. 24, 2016

(51) Int. Cl.
| | |
|---|---|
| A61K 31/41 | (2006.01) |
| A61K 9/20 | (2006.01) |
| A61K 9/00 | (2006.01) |

(52) U.S. Cl.
CPC ............ *A61K 31/41* (2013.01); *A61K 9/0065* (2013.01); *A61K 9/205* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 9/2086* (2013.01)

(58) Field of Classification Search
None
See application file for complete search history.

(56) References Cited

U.S. PATENT DOCUMENTS

| | | | |
|---|---|---|---|
| 4,803,081 A | 2/1989 | Falk et al. | |
| 4,973,469 A | 11/1990 | Mulligan et al. | |
| 5,736,161 A | 4/1998 | Garces et al. | |
| 5,780,057 A | 7/1998 | Conte et al. | |
| 5,945,125 A | 8/1999 | Kim | |
| 5,972,389 A | 10/1999 | Shell et al. | |
| 6,022,562 A | 2/2000 | Autant et al. | |
| 6,107,276 A | 8/2000 | Carli et al. | |
| 6,120,803 A | 9/2000 | Wong et al. | |
| 6,340,475 B2 | 1/2002 | Shell et al. | |
| 6,383,471 B1 | 5/2002 | Chen et al. | |
| 6,465,502 B1 | 10/2002 | Bullock et al. | |
| 6,630,475 B2 | 10/2003 | Neustadt et al. | |
| 6,635,280 B2 | 10/2003 | Shell et al. | |
| 6,692,767 B2 | 2/2004 | Burnside et al. | |
| 6,699,503 B1 | 3/2004 | Sako et al. | |
| 6,723,340 B2 | 4/2004 | Gusler et al. | |
| 6,881,420 B2 | 4/2005 | Flashner-Barak et al. | |
| 7,157,100 B2 | 1/2007 | Doshi et al. | |
| 7,728,021 B2 | 6/2010 | Dalmases Barjoan et al. | |
| 2001/0018070 A1 | 8/2001 | Shell et al. | |
| 2003/0152622 A1 | 8/2003 | Louie-Helm et al. | |
| 2003/0158244 A1 | 8/2003 | Devane et al. | |
| 2003/0180352 A1 | 9/2003 | Patel et al. | |
| 2003/0232081 A1 | 12/2003 | Doshi et al. | |
| 2004/0001888 A1 | 1/2004 | Jin | |
| 2005/0013863 A1 | 1/2005 | Lim et al. | |
| 2005/0096365 A1 | 5/2005 | Fikstad et al. | |
| 2006/0281801 A1 | 12/2006 | Kumar et al. | |
| 2007/0166372 A1 | 7/2007 | Huang et al. | |
| 2010/0233253 A1 | 9/2010 | Kavimandan et al. | |
| 2010/0291225 A1 | 11/2010 | Fanda et al. | |
| 2011/0027358 A1 | 2/2011 | Kshirsagar et al. | |
| 2011/0028456 A1* | 2/2011 | Lulla ..................... A61K 9/146 514/220 |
| 2011/0171275 A1 | 7/2011 | Jiang et al. | |
| 2012/0195968 A1 | 8/2012 | Shah et al. | |
| 2013/0136795 A1 | 5/2013 | Barrero et al. | |
| 2014/0371282 A1 | 12/2014 | Pilgaonkar et al. | |

FOREIGN PATENT DOCUMENTS

| | | |
|---|---|---|
| WO | 9907342 A1 | 2/1999 |
| WO | 0122791 A2 | 4/2001 |
| WO | 03000294 A1 | 1/2003 |
| WO | 03039521 A1 | 5/2003 |
| WO | 2006113631 A2 | 10/2006 |
| WO | 2007077581 A2 | 7/2007 |
| WO | 2008064338 A2 | 5/2008 |
| WO | 2008084504 A2 | 7/2008 |
| WO | 2009084040 A1 | 7/2009 |
| WO | 2009135646 A2 | 11/2009 |

OTHER PUBLICATIONS

L. H.V. Reddy and R.S.R. Murthy, "Floating Dosage Systems in Drug Discovery," Critical Reviews in Therapeutic Drug Carrier Systems (2002) 19(6): 553-585. Abstract Only.
Colorcon, Opadry II, 2009.
The National Formulary 24, United States Pharmacopeia 29 <711> 2673 (United States Pharmacopeial Convention 2006).
Don C. Cox & William B. Furman, Systematic Error Associated with Apparatus 2 of the USP Dissolution Test I: Effects of Physical Alignment of the Dissolution Apparatus, 71 J. Pharm. Scis. 451 (1982).
Don C. Cox et al., Systematic Error Associated with Apparatus 2 of the USP Dissolution Test III: Limitations of Calibrators and the USP Suitability Test, 72 J. Pharm. Scis. 910 (1983).
Saeed A. Qureshi & Iain J. McGilveray, Typical variability in drug dissolution testing: study with USP and FDA calibrator tablets and a marketed drug (glibenclamide) product, 7 Eur. J. Pharm. Scis. 249 (1999).
Saeed A. Qureshi & Javad Shabnam, Cause of high variability in drug dissolution testing and its impact on setting tolerances, 12 Eur. J. Pharm. Scis. 271 (2001).

(Continued)

Primary Examiner — Jessica Worsham
(74) Attorney, Agent, or Firm — Amin Talati Upadhye LLP; Adam D. Sussman; Yichen Cao

(57) ABSTRACT

The present invention provides extended release pharmaceutical formulations of valsartan with controlled impurity levels. Particularly, the present invention provides extended release valsartan formulation which is substantially free of valsartan R-isomer impurity.

5 Claims, No Drawings

(56) References Cited

OTHER PUBLICATIONS

Paulo Costa & J.M. Sousa Lobo, Influence of Dissolution Medium Agitation on Release Profiles of Sustained-Release Tablets, 27 Drug Development & Industrial Pharmacy 811 (2001).

J. Kukura et al., Shear distribution and variability in the USP Apparatus 2 under turbulent conditions, 279 Int'l J. Pharmaceutics 9 (2004).

Jennifer L. Baxter et al., Hydrodynamics-induced variability in the USP apparatus II dissolution test, 292 Int'l J. Pharmaceutics 17 (2005).

Ge Bai et al., Hydrodynamic Investigation of USP Dissolution Test Apparatus II, 96 J. Pharm. Scis. 2327 (2007).

Ge Bai & Piero M. Armenante, Hydrodynamic, Mass Transfer, and Dissolution Effects Induced by Tablet Location during Dissolution Testing, 98 J. Pharm. Scis. 1511 (2009).

Piero Armenante & Fernando Muzzio, Inherent Variability in Dissolution Testing: The Effect of Hydrodynamics in the USP II Apparatus (2005), available at http://www.fda.gov/ohrms/dockets/ac/05/briefing/2005-4187B1_01_04-Effect-Hydrodynamics.pdf.

* cited by examiner

EXTENDED RELEASE PHARMACEUTICAL FORMULATIONS WITH CONTROLLED IMPURITY LEVELS

FIELD OF THE INVENTION

The present invention provides extended release pharmaceutical formulations of valsartan with controlled impurity levels. Particularly, the present invention provides extended release valsartan formulation which is substantially free of valsartan R-isomer impurity.

BACKGROUND OF THE INVENTION

Valsartan is a potent, orally active nonpeptide tetrazole derivative that selectively inhibits angiotensin II receptor type 1. By blocking the action of angiotensin, valsartan causes reduction in blood pressure and is therefore used in treatment of hypertension, congestive heart failure and post-myocardial infarction. Valsartan also known as (S)—N-(1-oxopentyl)-N-[[2'-(1H-tetrazol-5-yl) [1,1'-biphenyl]-4-yl] methyl]-L-valine or N-[p-(o-1H-tetrazol-5-ylphenyl)benzyl]-N-valeryl-L-valine, has the following structure and is marketed as the free acid under the name DIOVAN.

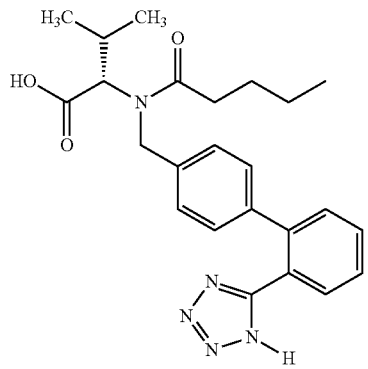 [SMILES: CCCCC(=O)N(Cc1ccc(-c2ccccc2-c2nnn[nH]2)cc1)[C@H](C(=O)O)C(C)C]

DIOVAN is prescribed as immediate release oral tablets in dosages of 40 mg, 80 mg, 160 mg and 320 mg of valsartan.

The quality and safety of pharmaceuticals can be significantly affected by the presence of impurities. Consequently, testing and controlling generation of impurities in the active pharmaceutical ingredient (API) during synthesis and in the pharmaceutical product during manufacture becomes imperative. Likewise, the presence of impurities in valsartan formulation may affect its safety and shelf life. USP monograph for valsartan describes two liquid chromatographic determinations for limiting a total of three related compounds, valsartan related compounds A, B and C. Valsartan related compound A having the following structure, is the R-enantiomer of valsartan and is chemically known as (R)—N-valeryl-N-([2'-(1H-tetrazole-5-yl) biphen-4-yl] methyl)-valine. It is generated by isomerization of valsartan S-isomer and is commonly referred to as Impurity A.

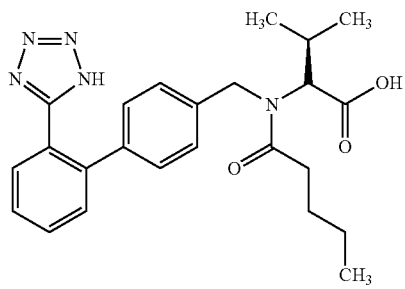

Various attempts have been made to control the levels of valsartan R-isomer impurity in valsartan during synthesis and provide an enantiomeric excess of S-valsartan. U.S. Pat. No. 7,728,021 and US2006/0281891 discuss processes for obtaining valsartan in substantially pure enantiomeric form. Though attempts have been made to provide valsartan API with an enantiomeric excess of S-isomer, not many attempts have been made to control generation of valsartan impurity A during the preparation of pharmaceutical formulations. WO2009/135646 discusses an immediate release formulation of valsartan wherein filler such as solid sugar alcohol consisting of mannitol, xylitol, maltitol, sorbitol, lactitol, erythritol, isomalt and mixtures thereof is employed. The solid sugar alcohols have been discussed to shorten the wet granulation process because less drying time is needed to achieve a residual humidity suitable for tabletting and thereby provide formulations with an impurity profile which is better since tablets are for less time under stressful conditions.

However, attempts have not been made to control the levels of impurity A in controlled release pharmaceutical formulations of valsartan.

The absolute bioavailability of valsartan is about 25%. Pharmaceutically active agents which exhibit low bioavailability unfortunately create a need for frequent dosing of a large amount of the active agent in order to provide and maintain therapeutic levels. The need for frequent dosing presents patient compliance problems. Attempts have therefore been made to deliver valsartan in an extended release form. Further, since the relatively low bioavailability of valsartan is primarily due to its poor solubility in the acid milieu of the stomach, attempts have been made to improve the bioavailability of valsartan by incorporation of solubilizers in the formulations.

WO2009/084040 discusses controlled release once a day formulation of valsartan in the form of a gastroretentive dosage form comprising solubilized active agent. Such formulations however have been identified to have increased levels of impurity A which is not desirable. Incorporation of solubilizers to improve the solubility and bioavailability of valsartan necessitates treating valsartan with solubilizers by different methods and at different temperature and time conditions. Such treatments tend to result in the generation of impurity A in the formulations, thereby presenting a need to monitor and control valsartan R-isomer impurity when preparing extended release pharmaceutical formulations, particularly extended release formulations comprising solubilizers.

The present inventors after rigorous studies provide extended release formulations of valsartan which are substantially free of valsartan R-isomer. The present inventors provide extended release formulations comprising valsartan, at least one solubilizer, at least one release modifier and at least one pharmaceutically acceptable excipient; wherein valsartan is completely or partially solubilized with the solubilizer at controlled solubilization conditions to provide formulations which are substantially free of valsartan R-isomer.

SUMMARY OF THE INVENTION

The present invention provides extended release pharmaceutical formulations of valsartan with controlled impurity levels. Particularly, the present invention provides extended release valsartan formulation which is substantially free of valsartan R-isomer impurity. The present invention further relates to extended release formulations comprising valsartan, at least one solubilizer, at least one release modifier and at least one pharmaceutically acceptable excipient; wherein the formulation is substantially free of valsartan R-isomer.

DETAILED DESCRIPTION OF THE INVENTION

The present invention provides extended release formulations of valsartan which are substantially free of valsartan R-isomer impurity. The term "substantially free" as used herein refers to extended release formulations comprising not more than about 1% by weight of the valsartan R-isomer impurity. In another embodiment, the extended release formulations of the present invention comprise not more than about 0.8% by weight of the valsartan R-isomer impurity. In a further embodiment, the extended release formulations of the present invention comprise not more than about 0.7% by weight of the valsartan R-isomer impurity.

The term "composition" or "formulation" or "dosage form" has been employed interchangeably for the purpose of the present invention and means that it is a pharmaceutical formulation which is suitable for administration to a patient. For the purpose of the present invention, the terms "controlled release" or "sustained release" or "extended release" or "modified release" or "prolonged release" have been used interchangeably and mean broadly that the active agent is released at a predetermined rate that is different or slower than immediate release of the active agent.

In one embodiment, the present invention provides extended release pharmaceutical formulations comprising valsartan and at least one solubilizer; wherein the formulation is substantially free of valsartan R-isomer impurity. In a further embodiment, the present invention provides extended release pharmaceutical formulations comprising valsartan, at least one solubilizer, at least one release modifier and at least one pharmaceutically acceptable excipient; wherein the formulation is substantially free of valsartan R-isomer.

In one embodiment, valsartan employed in the formulations of the present invention is in the form of salts, esters, amides, prodrugs, active metabolites, analogs, and the like. In a further embodiment, valsartan in crystalline, substantially crystalline, amorphous, substantially amorphous, dissolved or solubilized form and the like or any combinations thereof may be employed. In another embodiment, the crystalline form of valsartan may have different polymorphs. All different polymorphs, solvates, hydrates, salts of valsartan are within the purview of this invention. The term "substantially" referred to herein with respect to the form of the active means not less than 90% of the active is present in that active form. In one embodiment, valsartan is present in the formulations of the present invention in a substantially amorphous form. In one embodiment, valsartan is employed in the formulations of the present invention in an amount typically ranging from about 40 mg to about 640 mg. In a further embodiment, the amount of valsartan employed in the formulations of the present invention is from about 40 mg to about 320 mg. In another embodiment, the amount of valsartan employed in the formulations of the present invention is from about 80 mg to about 320 mg.

In one embodiment, the present invention provides extended release pharmaceutical formulations comprising valsartan, at least one solubilizer, and at least one pharmaceutically acceptable excipient; wherein (i) valsartan is completely or partially solubilized using one or more solubilizers and (ii) the formulation is substantially free of valsartan R-isomer. In another embodiment, the present invention provides extended release pharmaceutical formulations comprising valsartan, at least one solubilizer, at least one release modifier and at least one pharmaceutically acceptable excipient; wherein (i) valsartan is completely or partially solubilized using one or more solubilizers and (ii) the formulation is substantially free of valsartan R-isomer. In a still further embodiment, the present invention further provides extended release pharmaceutical formulations comprising valsartan, at least one solubilizer, at least one release modifier and at least one pharmaceutically acceptable excipient; wherein (i) valsartan is completely or partially solubilized using one or more solubilizers at controlled solubilization conditions and (ii) the formulation is substantially free of valsartan R-isomer.

In one embodiment, one or more solubilizers employed in the compositions of the present invention may be polymeric or non-polymeric in nature. In a further embodiment, one or more solubilizers include, but are not limited to, cationic, anionic, zwitterionic, nonionic, hydrophilic, hydrophobic or amphiphilic surfactants and the like or any combinations thereof. The ionic surfactants include, but are not limited to, alkylammonium salts; fusidic acid salts; fatty acid derivatives of amino acids, oligopeptides, or polypeptides; glyceride derivatives of amino acids; lecithins or hydrogenated lecithins; lysolecithins or hydrogenated lysolecithins; phospholipids or derivatives thereof; lysophospholipids or derivatives thereof; carnitine fatty acid ester salts; salts of alkylsulfates; fatty acid salts; sodium docusate; acyl lactylates; mono- or di-acetylated tartaric acid esters of mono- or di-glycerides; succinylated mono- or di-glycerides; citric acid esters of mono- or di-glycerides; or mixtures thereof. The amphiphilic surfactants include, but are not limited to, d-a-tocopheryl polyethylene glycol 1000 succinate and d-a-tocopherol acid salts such as succinate, acetate, etc. The non-ionic surfactants include, but are not limited to, fatty plcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols or sterol derivatives; polyethylene glycol alkyl ethers; sugar esters; sugar ethers; lactic acid derivatives of mono- or diglycerides; oil-soluble vitamins/vitamin derivatives; PEG fatty acid esters; polyglycerized fatty acid; polyoxyethylene-polyoxypropylene block copolymers; transesterification products of a polyol with at least one member of the group consisting of glycerides, vegetable oils, hydrogenated vegetable oils, fatty acids and sterols wherein the commonly used oils are castor oil or hydrogenated castor oil, or an edible vegetable oil such as corn oil, olive oil, peanut oil, palm kernel oil, almond oil and the commonly used polyols include glycerol, propylene glycol, ethylene glycol, polyethylene glycol, sorbitol and pentaerythritol; or mixtures thereof. In another embodiment of the present invention, the one or more solubilizers that may be employed include polyethylene-polyoxypropylene block copolymer (Lutrol® series BASF) and d-a-tocopheryl polyethylene glycol 1000 succinate (Vitamin E 25 TPGS® by Eastman) or combinations thereof.

In one embodiment, in the compositions of the present invention valsartan and one or more solubilizers may be employed in different ratios. It is contemplated within the scope of the invention that the ratio of valsartan to solubilizers may range from about 50:1 to about 1:50. In one embodiment, the ratio of valsartan to solubilizers is from about 20:1 to about 1:20. In another embodiment, the ratio of valsartan to solubilizer is from about 10:1 to about 1:10.

In an embodiment, the one or more solubilizers include, but are not limited to, PEG-20-glyceryl stearate, PEG-40 hydrogenated castor oil, PEG-6 corn oil, lauryl macrogol-32 glyceride, stearoyl macrogol glyceride, polyglyceryl-10 monodioleate, propylene glycol oleate, propylene glycol dioctanoate, propylene glycol caprylate/caprate, glyceryl monooleate, glycerol monolinoleate, glycerol monostearate, PEG-20 sorbitan monolaurate, PEG-4 lauryl ether, sucrose distearate, sucrose monopalmitate, polyoxyethylene-polyoxypropylene block copolymer, polyethylene glycol 660 hydroxystearate, sodium lauryl sulphate, sodium dodecyl sulphate, propylene glycol alginate, sodium taurocholate, sodium glycocholate, sodium deoxycholate, betains, polyethylene glycol, d-alpha-tocopheryl polyethylene glycol 1000 succinate, and mixtures thereof.

In a further embodiment, valsartan is treated with one or more solubilizers. In another embodiment, valsartan is completely or partially solubilized using one or more solubilizers. In one embodiment, valsartan is completely or partially solubilized using one or more solubilizers at controlled solubilization conditions. The term "solubilized" as used herein refers to improved or increased solubility form of valsartan. "Improved or increased solubility form of valsartan" refers to a form of valsartan wherein valsartan is intimately dispersed in at least one solubilizer, and the dissolution of valsartan there from is not less than about 30% in 0.1N HCl in 30 minutes. In a further embodiment, the dissolution of valsartan there from is not less than about 50% in 0.1N HCl in 30 minutes. In another embodiment, the dissolution of valsartan there from is not less than about 70% in 0.1N HCl in 30 minutes. The term "completely or partially" as used herein refers to whether the entire or part of the valsartan dose is solubilized.

It is contemplated within the scope of the invention that the processes employed for solubilization of valsartan may include but are not limited to melt granulation, solvent treatment, wet granulation, physical mixing or spray drying and the like or combinations thereof. In one embodiment valsartan may be completely or partially solubilized using the melt granulation method. In the case of melt granulation, the solubilizer is melted. Valsartan is then added and mixed with the molten mass, and allowed to solidify to prepare granules. In another embodiment the solubilizers are melted. Valsartan is then added and mixed with the molten mass. This blend is further mixed with diluents, acidulants, disintegrants and the like or mixtures thereof, capable of converting this semisolid mass into dry powder. Non limiting examples of diluents include, but are not limited to, celluloses such as microcrystalline cellulose, silicon dioxide, silicates, magnesium aluminium silicate, calcium silicate, and the like or mixtures thereof. Non-limiting examples of acidulants include, but are not limited to, fumaric acid, citric acid and the like or mixtures thereof. Non-limiting examples of disintegrants include, but are not limited to, crospovidone, croscarmellose sodium and the like or mixtures thereof. In another illustrative embodiment of this system, valsartan is granulated using a molten solubilizer. In another embodiment, valsartan and the solubilizer both may be heated together and congealed to room temperature. In another embodiment, valsartan may be solubilized using solvent treatment method. In the case of solvent treatment method, either the solubilizer or valsartan or both are dissolved in a solvent which is then removed using different methods, such as but not limited to, evaporation, spray drying or the like or combinations thereof. The resultant mass comprises a blend of valsartan and solubilizer. The solvent employed in this system may be aqueous or non-aqueous. In a further embodiment, valsartan may be solubilized using physical mixing. Valsartan may be intimately dry-mixed using a low shear granulator, a V-blender, or a high shear granulator. In a further embodiment, valsartan may be treated with one or more solubilizer by wet granulation. In another embodiment, valsartan may be solubilized with one or more solubilizers by spray drying. In one embodiment, the method of solubilization of valsartan employed is melt granulation. It is contemplated within the scope of the invention that a combination of aforementioned processes can be employed for treating valsartan with solubilizers. It is also contemplated within the scope of the invention that any process known in the art suitable for making pharmaceutical compositions in general may be employed for the purpose of this invention.

Without being bound to any theory it is believed that the process of solubilization of valsartan causes the generation of valsartan R-isomer impurity. Studies involving exposure of valsartan active ingredient to varying temperatures indicate that valsartan R-isomer impurity is not generated when the active as such is exposed to increased temperatures. However, valsartan R-isomer impurity is generated when valsartan is dispersed in or is intimately mixed with at least one solubilizer at certain temperature ranges for prolonged time periods. In one embodiment, valsartan R-isomer impurity is generated when valsartan is dispersed in or is intimately mixed with at least one molten solubilizer at specific temperature ranges for certain time periods. It is believed that valsartan S-isomer when intimately dispersed in at least one solubilizer at high temperatures of about 75° C. or higher for prolonged time periods of more than about 15 minutes during the solubilization process gets the necessary medium and energy to undergo isomerization to give the valsartan R-isomer. The exposure of valsartan to high temperature during the solubilization process could be due to direct exposure thereof to thermal energy or conversion of other forms of energy to thermal energy. In a further embodiment, it is believed that solubilizers provide necessary medium for isomerization, higher temperature provides sufficient energy for conversion of S-isomer into R-isomer and with prolonged exposure to higher temperature conditions the amount of R-isomer impurity generated is further increased.

In one embodiment, the process of solubilizing valsartan is therefore carried out at controlled time and temperature conditions. Controlled time and temperature conditions appear not to provide sufficient energy necessary for conversion of valsartan S-isomer to the R-form thereby reducing the generation of the R-impurity and providing extended release pharmaceutical formulations that are substantially free of the R-isomer. The present invention relates to an extended release pharmaceutical formulation comprising valsartan which is completely or partially solubilized with the solubilizer at controlled solubilization conditions.

In a further embodiment, the process of solubilization of valsartan is carried out at a temperature of not more than about 75° C. In another embodiment, in the process of solubilization of valsartan with solubilizer, valsartan may be exposed to temperatures of not more than about 75° C. In one embodiment, when the process of solubilization is melt granulation process, the product bed temperature is maintained at about 35° C. to about 75° C. In another embodiment, the process of solubilization of valsartan is carried out at a temperature of not more than about 75° C. for a time period of about 15 seconds to about 60 minutes. In one embodiment, the process of solubilization of valsartan is carried out at a temperature of not more than about 75° C. for a time period of about 15 seconds to about 30 minutes. In a further embodiment, the process of solubilization of valsartan is carried out at a temperature of not more than about 75° C. for a time period of about 1 minute to about 30 minutes. In yet another embodiment, the process of solubilization of valsartan is carried out at a temperature of not more than about 75° C. for a time period of about 5 minutes to about 30 minutes. The solubilized valsartan formed with such controlled temperature and time conditions during melt granulation controls the levels of impurity A to be within desired limits.

In a further embodiment, release modifiers employed in the extended release formulations of the present invention include, but are not limited to, polymeric release retardants, non-polymeric release retardants or any combinations thereof. In another embodiment, swelling or non-swelling type of release retardants may be employed in the compositions of the present invention. Release modifiers are employed in the compositions of the present invention to control the release of valsartan and/or solubilized valsartan. Polymeric release modifiers employed for the purpose of the present invention include, but are not limited to, cellulose derivatives; cross-linked polyvinyl pyrrolidone, polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. Cellulose derivatives include, but are not limited to, ethyl cellulose, methylcellulose, hydroxypropylmethylcellulose (HPMC), hydroxypropyl cellulose (HPC), hydroxyethyl cellulose, hydroxymethyl cellulose, hydroxypropyl ethylcellulose, carboxymethylethyl cellulose, carboxy-ethylcellulose, carboxymethyl hydroxyethylcellulose, hydroxyethylmethyl carboxymethyl cellulose, hydroxyethyl methyl cellulose, carboxymethyl cellulose (CMC), methylhydroxyethyl cellulose, methylhydroxypropyl cellulose, carboxymethyl sulfoethyl cellulose, sodium carboxymethyl cellulose, or combinations thereof. In one embodiment, polymeric release retardants of one or more different viscosities may be employed. In a further embodiment, the release modifier employed in the extended release formulations of the present invention is hydroxypropyl methyl cellulose. Non-polymeric release modifiers employed for the purpose of the present invention include, but are not limited to, fats, oils, waxes, fatty acids, fatty acid esters, long chain monohydric alcohols and their esters or combinations thereof. The amount of release modifier in the dosage form generally varies from about 5% to about 90% by weight of the dosage form.

In another embodiment, the pharmaceutically acceptable excipients that may be employed in the compositions of the present invention include but are not limited to, acid source, gas generating agents, binders, lubricants, diluents, disintegrants, glidants, colorants, pH modifiers, pore-formers, and the like or mixtures thereof.

In a further embodiment, acidulants may be employed in the compositions of the present invention. Non-limiting examples of acidulants that may be employed in the compositions of the present invention include aliphatic or aromatic, saturated or unsaturated, monobasic acid (monocarboxylic acid), dibasic acid (dicarboxylic acid) or tribasic acid (tricarboxylic acid). In one embodiment of the present invention, the acidulant is malic acid, tartaric acid, fumaric acid, maleic acid, aspartic acid or. citric acid and the like or any combinations thereof. The acidulants also function as acid source when with the gas generating agent as an effervescent couple. In a further embodiment, the pharmaceutical composition of the present invention may comprise at least one gas generating agent. The gas generating agents also referred to as effervescent agent aid in the formation of highly porous, preferably honeycombed structure and enhances the buoyancy of the formulation. The gas generating agent employed for the purpose of the present invention is selected from, but not limited to, alkali and alkaline-earth metal carbonates and bicarbonates such as sodium bicarbonate, sodium glycine carbonate, potassium bicarbonate, ammonium bicarbonate, sodium bisulfite, sodium metabisulfite, sodium carbonate, potassium carbonate and the like or combinations thereof. In one embodiment, the gas generating agent is used at concentration from about 0.5 weight % to about 25 weight % of the dosage form.

Non-limiting examples of suitable binders that may be employed in the compositions of the present invention include, but are not limited to, starch, pregelatinized starch, polyvinyl prrolidone (PVP), copovidone, cellulose derivatives, such as hydroxypropylmethyl cellulose (HPMC), hydroxypropyl cellulose (HPC), carboxymethyl cellulose (CMC) and their salts and the like or combinations thereof. Non-limiting examples of diluents that may be employed in the compositions of the present invention include, but are not limited to, starch, dicalcium phosphate, microcrystalline cellulose, lactose monohydrate, dextrate hydrated and the like or combinations thereof. Suitable lubricants that may be employed include, but are not limited to, magnesium stearate, calcium stearate, stearic acid, talc, sodium stearyl fumarate and the like or combinations thereof. Non-limiting examples of glidants that may be employed include, but are not limited to, colloidal silica, colloidal silicon dioxide, silica gel, precipitated silica, and the like or combinations thereof. Suitable pore forming agents such as, but not limited to, dextrates, non-GMO dextrates, lactose, sodium chloride, and the like or combinations may be employed in the formulations of the present invention. Suitable adsorbents that may be used in the formulations of the present invention, include but are not limited to, silicates such as aluminum magnesium metasilicate, calcium silicate, and the like; microcrystalline celluloses and the like or combinations thereof. Suitable colorants such as, but not limited to, ferric oxide (Sicovit Red 30 E172) may be employed in the compositions of the present invention. Disintegrating agents such as, but not limited to, starch, sodium starch glycolate, pregelatinised starch, crosslinked polyvinyl pyrrolidone, crosslinked carboxy methylcellulose, or ion exchange resin, may be employed in the composition if required. In one embodiment, disintegrating agents as listed herein above may be employed in the compositions of the present invention to improve the dissolution.

In a further embodiment, the formulation of the present invention is in the form of an extended release formulation.

In another embodiment the extended release formulation of the present invention is in the form of a gastroretentive dosage form. For the purpose of the present invention the term "gastroretentive" or "gastric retention" or "gastroretention" or "retained in upper gastrointestinal tract" when used with respect to the dosage form of the present invention, means that the dosage form or at least a portion thereof remains in the upper gastrointestinal tract including stomach, for about 30 minutes or more. In another embodiment, the gastroretentive• dosage form of the present invention remains in the upper gastrointestinal tract including stomach, for about 30 minutes to about 12 hours. In another embodiment controlled release formulation of the present invention is in the form of a gastroretentive dosage form. In a further embodiment, gastroretentive dosage forms that are retained in the upper gastrointestinal tract for a prolonged period of time after oral administration and release the active ingredient continuously at a predetermined rate or in a sustained manner are employed for delivering valsartan.

In one embodiment, the gastroretentive extended release formulation of the present invention further in addition to valsartan, at least one solubilizer, at least one release modifier and at least one pharmaceutically acceptable excipient, further comprises at least one swelling agent, and at least one swelling enhancer.

In one embodiment, the swelling polymers employed in the dry state or in a form that has substantial capacity for water uptake may be employed in the compositions of the present invention. Non-limiting examples of such swelling polymers employed in the present invention include, but are not limited to, polyalkylene oxides; cellulosic polymers; acrylic acid and methacrylic acid polymers, and esters thereof, maleic anhydride polymers; polymaleic acid; poly(acrylamides); poly(olefinic alcohol)s; poly(N-vinyl lactams); polyols; polyoxyethylated saccharides; polyoxazolines; polyvinylamines; polyvinylacetates; polyimines; starch and starch-based polymers; polyurethane hydrogels; chitosan; polysaccharide gums; alginates; zein; shellac-based polymers; polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch and polyvinyl alcohol, and the like or mixtures thereof. In a further embodiment one or more swelling polymers employed for the purpose of the present invention include, but are not limited to, polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch, polyvinyl alcohol and the like or mixtures thereof. In another embodiment, the weight percent of the swelling polymer in the final compressed dosage form is about 5 to about 95 weight percent.

In one embodiment, the swelling enhancers that may be employed in the composition of the present invention include, but are not limited to, low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch, sodium carboxymethyl starch and the like or combinations thereof. In another embodiment, the content of the swelling enhancer that may be employed is about 5 to about 90 weight percent of the formulation. At concentration above about 5% w/w the non-limiting list of agents listed above function as swelling enhancers and help swelling polymers to swell rapidly.

In a further embodiment, the gastroretentive dosage form of the present invention may be in the form of a monolithic system, an expanding bilayered or multilayered or in-lay system for oral administration which is adapted to deliver the drug at a predetermined rate. In one embodiment, valsartan is incorporated in monolithic matrix type of extended release gastroretentive formulation. In another embodiment, valsartan is incorporated in a bilayered gastroretentive dosage form that consists of a drug layer and a gastroretentive expanding layer wherein the drug is released at a predetermined rate from the drug layer. In a further embodiment pharmaceutical controlled release gastroretentive composition in the form of an expanding bilayered system for oral administration is provided to deliver valsartan from a first layer immediately upon reaching the gastrointestinal tract, and to deliver same or different active, from a second layer, in a sustained manner over a specific time period. The second layer is also adapted to provide expanding nature for the dosage system, thereby making the dosage system have greater retention in the stomach.

In yet another illustrative embodiment according to the invention, the extended release formulation with improved bioavailability may be optionally coated. Surface coatings may be employed for aesthetic purposes or for dimensionally stabilizing the dosage form. The coating may be carried out using any conventional technique employing conventional ingredient. A surface coating can, for example, be obtained using a quick-dissolving film using conventional polymers such as, but not limited to, hydroxypropyl methyl cellulose, hydroxypropyl cellulose, carboxymethyl cellulose, ethyl cellulose, polyvinyl alcohol, polymethacrylates or the like or combinations thereof. Tablets of the present invention may vary in shape including, but not limited to, oval, triangle, almond, peanut, parallelogram, pentagonal. It is contemplated within the scope of the invention that the dosage form can be encapsulated. Tablets in accordance with the present invention may be manufactured using conventional techniques of common tableting methods known in the art such as direct compression, dry granulation, wet granulation and extrusion melt granulation.

Further, in one embodiment, the present invention provides a process of preparing an extended release formulation comprising: preparing solubilized valsartan by solubilization using with one or more solubilizer; blending said solubilized valsartan with at least one release modifier, and at least one pharmaceutically acceptable excipient; lubricating the blend to form a lubricated blend; compressing the blend to form a monolithic tablet. In another embodiment, the present invention provides a process of preparing an extended release gastroretentive formulation comprising: preparing solubilized valsartan by solubilization using one or more solubilizers; blending said solubilized valsartan with at least one release modifier, at least one swelling polymer• and at least one pharmaceutically acceptable excipient; lubricating the blend to form a lubricated blend; compressing the blend to form a monolithic tablet. Furthermore, the present invention also provides a process of preparing an extended release gastroretentive dosage form of valsartan comprising: preparing solubilized valsartan by solubilization using one or more solubilizers; blending said solubilized valsartan with at least one release modifier and at least one pharmaceutically acceptable excipient, lubricating the blend to form drug layer blend; blending at least one swelling polymer, at least one pharmaceutically acceptable excipient, lubricating the blend to form a gastroretentive layer blend; and compressing the drug layer and the gastroretentive layer to form a bilayer tablet. In one embodiment, the extended compositions of the present invention are in the form of bilayered gastroretentive dosage form comprising the active layer and the gastroretentive layer. In a further embodiment, the extended release formulation of the present invention is prepared by (i) melting the solubilizer, (ii) adding valsartan to the molten solubilizer, (iii) intimately dispersing valsartan with molten solubilizer at controlled solubilization conditions, (iv) adding diluents to the molten mass and mixing, (v) cooling the granules formed, (vi) blending with at least one release modifier and at least one pharmaceutically acceptable excipient with the granules (vii) lubricating the blend to form an active layer blend (viii) blending and granulating part of at least one swelling polymer, at least one swelling enhancer and at least one pharmaceutically acceptable excipient; (ix) blending the granules with remaining amounts of at least one swelling polymer, at least one swelling enhancer and at least one pharmaceutically acceptable excipient (x) lubricating the blend to form the gastroretentive layer blend (ix) compressing the drug layer blend and gastroretentive layer blend to form bilayered gastroretentive tablet dosage form.

In one embodiment, the solubilized valsartan is prepared under controlled solubilization conditions as discussed hereinbefore. In a further embodiment, the solubilized valsartan is prepared at a temperature of not more than about 75° C. as discussed hereinbefore.

In another embodiment, levels of impurity A studied for six months at 40° C./75% RH for the solubilized valsartan prepared by melt granulation at controlled temperature conditions as stated above indicated that impurity A levels are within the desired limits. In a further embodiment, the pharmaceutical compositions of the present invention are subjected to stability studies for 6 months at different temperatures and relative humidity (RH) conditions such as 25° C./60% RH, 40° C./75% RH and were found to be stable with controlled levels of impurity A.

In one embodiment, the extended release gastroretentive formulation of the present invention that may be coated or uncoated, single layered or multilayered dosage form gradually swells upon contact with the gastric fluid. The time taken for swelling may vary from about 15 minutes to about 4 hours. In a further embodiment, the time taken for swelling is within about 15 minutes to about 3 hours. In another embodiment, the time taken for swelling is within about 15 minutes to about 2 hours. Two dimensions of the dosage form namely length and width expand to more than about 8 mm after swelling within about 2 hours in media simulating typical gastric environment (0.1 N hydrochloric acid). In one embodiment, the length and width of the dosage form expand to more than about 10 mm after swelling within about 2 hours in media simulating typical gastric environment (0.1 N hydrochloric acid). In another embodiment, the length and width of the dosage form expand to more than about 12 mm after swelling within about 2 hours in media simulating typical gastric environment (0.1 N hydrochloric acid).

The extended release formulations according to the present invention allow for controlled release of valsartan. In one embodiment the valsartan is released over a period of more than about 4 hours. In a further embodiment the valsartan is released over a period of about 6 hours. In one embodiment the valsartan is released over a period of about 8 hours. In another embodiment the valsartan released over a period of about 12 hours. In another embodiment the valsartan released over a period of about 24 hours. In one embodiment, not more than about 40% vaslartan is released from the extended release formulations of the present invention in 1 hour and not less than 75% valsartan is released over 8 hours. Further, within the purview of the present invention, are included formulations that comprise a combination of valsartan with other drugs or active agents which may be delivered in an immediate release or modified release manner. In a further embodiment, the extended release pharmaceutical compositions of the present invention produce therapeutically desirable pharmacokinetic profiles in human subjects.

In one embodiment, the extended release formulations of the present invention exhibit pH dependent release of valsartan. In one embodiment, the release of valsartan from a 160 mg dosage form (Example 4) in 0.1 N HCl is not more than about 20% in thirty (30) minutes, not more than about 40% in one (1) hour, and about 60% in four (4) hours to about eight (8) hours.

In one embodiment, the extended release formulations of the present invention exhibit pH dependent release of valsartan. In one embodiment, the release of valsartan from a 160 mg dosage form (Example 4) in 0.001 N HCl is not more than about 20% in thirty (30) minutes, not more than about 40% in one (1) hour, and about 80% in four (4) hours to about eight (8) hours.

In one embodiment, the extended release formulations of the present invention exhibit pH dependent release of valsartan. In one embodiment, the release of valsartan from a 160 mg dosage form (Example 4) in 0.1 M acetate buffer (about pH 4.5) is not more than about 20% in thirty (30) minutes, not more than about 40% in one (1) hour, and about 100% in four (4) hours to about eight (8) hours.

In one embodiment, the extended release formulations of the present invention exhibit pH dependent release of valsartan. In one embodiment, the release of valsartan from a 160 mg dosage form (Example 4) in 0.05 M Tris buffer (about pH 6.8) is not more than about 20% in thirty (30) minutes, not more than about 40% in one (1) hour, and about 100% in four (4) hours to about eight (8) hours.

In one embodiment, the extended release formulations of the present invention may be combined with other anti-hypertensive agents. The additional anti-hypertensive agent may be delivered in immediate or extended release manner. In a further embodiment is provided the use of extended release pharmaceutical composition of valsartan of the present invention, which is substantially free of valsartan R-isomer impurity, for the manufacture of a medicament for treatment of hypertension and heart failure. In one embodiment, the present invention provides a method for treatment of hypertension and heart failure comprising administering to the subject in need thereof extended release pharmaceutical compositions of valsartan of the present invention, which is substantially free of valsartan R-isomer impurity. In another embodiment, the present invention provides a method for reducing the risk of fatal and nonfatal cardiovascular events, primarily strokes and myocardial infarctions, comprising administering to the subject in need thereof extended release pharmaceutical compositions of valsartan of the present invention, which is substantially free of valsartan R-isomer impurity.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

The invention is further illustrated by the following examples, which are for illustrative purposes and should not be construed as limiting the scope of the invention in any way.

EXAMPLES

Example 1: Compatibility Study for Valsartan Related Compound A (Valsartan R-Isomer Impurity)

Valsartan and valsartan solubilized in molten solubilizers as depicted in tables I and II respectively were subjected to compatibility studies at the following condition:

2 weeks 60° C. closed glass vial

TABLE I

| Sr. No. | Ingredients | Quantity/vial (mg) |
|---|---|---|
| 1. | Valsartan | 1000 |

TABLE II

| Sr. No | API and Excpients | Ratio Drug:Excipients |
|---|---|---|
| 1. | Valsartan:Kolliphor P 407 | 1:0.5 |
| 2. | Valsartan:Kolliphor TPGS | 1:0.5 |
| 3. | Valsartan:Kolliphor P 407: Kolliphor TPGS | 1:0.5:0.5 |

Solubilized valsartan used for the study was prepared by melting the solubiliser/s (Kolliphor P 407, Kolliphor TPGS and combination thereof) in a beaker at water bath temperature 65° C. The drug was mixed with the molten solubiliser/s uniformly at water bath temperature 65° C. and the cooled mass was used in the studies.

Levels of Impurity A were evaluated at the tabulated conditions as mentioned in Table III.

TABLE III

| Impurity | Initial | 2 Weeks 60° C. Closed glass Vial |
|---|---|---|
| Valsartan API | 0.03 | 0.05 |
| Valsartan and Kolliphor P 407 | 0.05 | 1.94 |
| Valsartan and Kolliphor TPGS | 0.04 | 2.2 |
| Valsartan and Kolliphor TPGS + Kolliphor P 407 | 0.26 | 2.38 |

This study indicated the following:
A) Valsartan R-isomer impurity (Impurity A) was not generated in valsartan API sample at the different conditions evaluated.
B) Valsartan R-isomer impurity (Impurity A) was generated in the valsartan and solubilizer/s samples. Increased levels of impurity A was found to be generated in the samples maintained at 60° C. for 2 weeks.

The above study indicates that impurity A is generated in samples comprising valsartan and solubilizers, when they are maintained at higher temperature condition for prolonged time period, while the valsartan API sample does not indicate such a generation and increase in the levels of valsartan impurity A.

Example 2: Evaluation of Impact of Solubilization Temperature on Impurity A Levels Table IV: Composition of Solubilized Valsartan

TABLE IV

| Composition of solubilized valsartan | |
|---|---|
| Ingredients | mg/tablet |
| Valsartan | 160 |
| Vitamin E Polyethylene Glycol Succinate (Kolliphor ® TPGS) | 80 |
| Poloxamer (Kolliphor ® P 407) | 80 |

Procedure:

Three sets of solubilized valsartan were prepared using the above excipients by maintaining the product bed at different temperatures.

1. Valsartan is added to molten poloxamer and Vitamin E polyethylene glycol succinate in a jacketed mixer and mixed well for 15 minutes.
2. The product bed temperature is maintained at 60° C. for set I, at 70° C. for set II and at 80° C. for set III of solubilized valsartan.

Three set of granules prepared at different temperature as depicted above were analyzed for impurity A levels.

TABLE V

| Process Parameters | 3075-153-160 (Set I solubilized active) | 3053-113-160 (Set II solubilized active) | 3024-105-160 (Set III solubilized active) |
|---|---|---|---|
| Product Temp (° C.) | 60 | 70 | 80 |
| Impurity A | 0.02 | 0.13 | 0.82 |

The above study indicates that valsartan related compound A impurity in the solubilized valsartan increases at higher processing temperature. When product bed temperature is about 80° C., higher amount of impurity A is generated in the solubilized valsartan prepared.

Example 3: Composition of Valsartan Extended Release Tablets 160 mg

TABLE VI

| Ingredients | mg/tablet |
|---|---|
| Active layer | |
| Val sartan | 160 |
| Vitamin E polyethylene glycol succinate | 80 |
| Poloxamer | 80 |
| Microcrystalline Cellulose | 135 |
| Hydroxypropyl methylcellulose | 110 |
| Calcium Silicate | 120 |
| Crospovidone | 35 |
| Fumaric Acid | 78 |

TABLE VI-continued

| Ingredients | mg/tablet |
|---|---|
| Dextrates | 60 |
| Colloidal Silicon Dioxide | 10 |
| Magnesium Stearate | 20 |
| Ferric Oxide | 2 |
| Gastroretentive layer | |
| Polyethylene Oxide | 119 |
| Hydroxypropyl methyl cellulose | 119 |
| Hydroxyethyl Cellulose | 59 |
| Crospovidone | 120 |
| Microcrystalline Cellulose | 29 |
| Polyvinylpyrrolidone | 33 |
| 1-vinyl-2-pyrrolidone and vinyl acetate copolymer | 13 |
| Sodium Bicarbonate | 33 |
| Anhydrous Citric Acid | 10 |
| Magnesium Stearate | 5 |
| Isopropyl Alcohol | q. s. |
| Purified Water # | q. s. |
| Weight of core tablet | 1430 |
| Film coating | 60 |
| Total weight of coated tablet | 1490 |

Procedure:

A) Valsartan is added to molten poloxamer and Vitamin E polyethylene glycol succinate in a low shear mixer and mixed well for about 15 minutes. The product temperature is maintained at 65° C.±10° C. Microcrystalline cellulose, calcium silicate, fumaric acid and crospovidone are added to above mass and mixed further to get a homogeneous blend. All other ingredients are added to above mass and granulated. The granules were dried and lubricated with magnesium stearate to form active layer blend.

B) Povidone was dissolved in IPA: water mixture with overhead stirring. Polyethylene oxide, hydroxyl propyl methyl cellulose, hydroxyethyl cellulose, crospovidone, and microcrystalline cellulose were passed through the sieve and dry mixed in rapid mixer. The binder solution was added to the dry mix and the mass was granulated and subsequently dried in a fluidized bed dryer to get desired loss on drying. Sized dried granules were blended with other excipients like lactose, microcrystalline cellulose, sodium bicarbonate and citric acid and then lubricated using magnesium stearate to form gastroretentive layer blend.

A bilayer gastroretentive tablet of valsartan was prepared by compressing the drug layer blend and the gastroretentive layer blend. The bilayered tablets were subsequently film coated.

Analysis: The granules of part A above were analyzed by HPLC for Impurity A levels and the results are as mentioned in the below table:

TABLE VI (A)

| Impurity | Initial impurity levels in granules |
|---|---|
| Valsartan Impurity A | 0.15% |
| Total impurities | 0.04% |

These granules of valsartan prepared under controlled solubilization conditions were found to have controlled levels of impurity A.

The tablets prepared under controlled solubilization conditions as mentioned above were subjected to stability studies for 6 months at 40° C./75% relative humidity (RH) and then analyzed by HPLC for impurity A levels. The tablets prepared under controlled solubilization conditions were found to be stable with controlled levels of impurity A.

TABLE VII

| Storage conditions | Pack Details | Impurity | Initial | 3M | 6M |
|---|---|---|---|---|---|
| 40° C./ 75% RH | 120 cc HDPE bottle with 38 mm CRC (30's count) | Valsartan Impurity A | 0.11% | 0.20% | 0.36% |
| | | Total Impurities | 0.03% | 0.15% | 0.24% |

Example 4. Coated Extended Release Formulations of Valsartan (160 mg Dose and 320 mg Dose)

Two embodiments of coated extended release formulations of valsartan having 160 mg and 320 mg respectively are depicted in Tables VIII and Table IX. Table VIII describes compositions of valsartan core tablets. One of the procedures suitable for preparing such core tablets has been presented in Example 3. Table IX describes compositions of the dual coating system. One of the procedures suitable for preparing such coating system has been presented in Example 4. The amount of ingredients listed in the Tables VI, VIII, and IX are for the purpose of demonstration and are not intended to limiting. The precise amount of each ingredient depicted in the Examples and Tables can be adjusted based on needs and requirements.

TABLE VIII

Compositions of valsartan core tablets (160 mg and 320 mg valsartan)

| Ingredients | mg/unit | mg/unit |
|---|---|---|
| Active layer | | |
| Valsartan | 160 | 320 |
| Vitamin E polyethylene glycol succinate | 80 | 160 |
| Poloxamer | 80 | 160 |
| Microcrystalline Cellulose | 135 | 270 |
| Hydroxypropyl methylcellulose | 110 | 220 |
| Calcium Silicate | 120 | 240 |
| Crospovidone | 35 | 70 |
| Fumaric Acid | 78 | 156 |
| Dextrates | 60 | 120 |
| Colloidal Silicon Dioxide | 10 | 20 |
| Magnesium Stearate | 20 | 40 |
| Ferric Oxide | 2 | 4 |
| Gastroretentive layer | | |
| Polyethylene Oxide | 119 | 238 |
| Hydroxypropyl methyl cellulose | 119 | 238 |
| Hydroxyethyl Cellulose | 59 | 118 |
| Crospovidone | 120 | 240 |
| Microcrystalline Cellulose | 29 | 38 |
| Polyvinylpyrrolidone | 33 | 66 |
| 1-vinyl-2-pyrrolidone and vinyl acetate copolymer | 13 | 26 |
| Sodium Bicarbonate | 33 | 66 |
| Anhydrous Citric Acid | 10 | 20 |
| Magnesium Stearate | 5 | 10 |
| Isopropyl Alcohol | q. s. | q. s. |
| Purified Water # | q. s. | q. s. |
| Total | 1430 | 2860 |

TABLE IX

Compositions of the dual coating systems

| Ingredients | mg/unit | mg/unit |
| --- | --- | --- |
| Valsartan core tablets | 1430 | 2860 |
| Seal coating | | |
| Opadry Clear 03K19229 | 15.00 | 30.00 |
| Isopropyl alcohol # | q.s. | q.s. |
| Purified water # | q.s. | q.s. |
| Film coating | | |
| Polyvinyl Alcohol-based Opadry 200 Blue 200F105000 | 45.00 | 90.00 |
| Purified water # | q.s. | q.s. |
| Excipients (imprinting material) | | |
| Opacode Black S-1-17823 | 0.104 | 0.208 |
| Isopropyl alcohol # | q.s. | q.s. |
| Total | 1490 | 2980 |

We claim:

1. An extended release pharmaceutical formulation, comprising:
    a core comprising
        (a) a therapeutically effective amount of valsartan of about 160 mg;
        (b1) alpha-tocopherol polyethylene glycol succinate in an amount of about 80 mg;
        (b2) polyoxyethylene polyoxypropylene block copolymer in an amount of about 80 mg;
        (c1) polyethylene oxide in an amount of about 120 mg;
        (c2) hydroxypropyl methylcellulose in an amount of about 230 mg;
        (c3) hydroxyethylcellulose in an amount of about 60 mg;
        (d) cross-linked polyvinyl pyrrolidone in an amount of about 150 mg;
        (e) dextrates in an amount of about 60 mg; and
        (f) a pharmaceutically acceptable carrier; and
    a dual coating system surround the core;
    wherein the formulation comprises not more than about 0.7% by weight of valsartan R-isomer impurity, wherein a process of solubilization of valsartan is carried out at a temperature between 60° C. and 70° C., and wherein valsartan is completely or partially solubilized with (b1) and (b2), and wherein the dual coating system comprises a seal coating layer contacting the core and a film coating layer contacting the seal coating layer.

2. The extended release formulation of claim 1, wherein the core further comprises
    (g) microcrystalline cellulose in an amount of about 160 mg.

3. The extended release formulation of claim 1, wherein valsartan is in crystalline form, substantially crystalline form, amorphous form, substantially amorphous form, or any mixture thereof.

4. The extended release formulation of claim 1, wherein valsartan is in substantially amorphous form.

5. The extended release formulation of claim 1, wherein the formulation comprises not more than about 0.7% by weight of valsartan R-isomer impurity at 40° C./75% RH for 6 months.

* * * * *

UNITED STATES PATENT AND TRADEMARK OFFICE
CERTIFICATE OF CORRECTION

| | | |
|---|---|---|
| PATENT NO. | : 9,687,475 B1 | Page 1 of 1 |
| APPLICATION NO. | : 15/080305 | |
| DATED | : June 27, 2017 | |
| INVENTOR(S) | : Joseph A. Fix et al. | |

It is certified that error appears in the above-identified patent and that said Letters Patent is hereby corrected as shown below:

In the Claims

In Claim 1, Column 18, Line 7, change "surround" to --surrounding--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*